United States Patent [19]

Hirano et al.

[11] Patent Number: 4,501,898
[45] Date of Patent: Feb. 26, 1985

[54] PHOTOGRAPHIC DEVELOPMENT INHIBITOR (1H- OR 2H-) INDAZOLYL HYDROQUINONE DERIVATIVES

[75] Inventors: Shigeo Hirano; Kei Sakanoue, both of Kanagawa, Japan

[73] Assignee: Fuji Photo Film Co., Ltd., Kanagawa, Japan

[21] Appl. No.: 384,809

[22] Filed: Jun. 3, 1982

Related U.S. Application Data

[62] Division of Ser. No. 259,278, Apr. 30, 1981, Pat. No. 4,345,024.

[30] Foreign Application Priority Data

Apr. 30, 1980 [JP]  Japan ................... 55-57270

[51] Int. Cl.³ .................. G03C 7/00; G03C 1/40; C07D 231/56
[52] U.S. Cl. .................. 548/336; 548/251; 548/300; 548/348; 548/371
[58] Field of Search ............... 548/371, 300, 327, 336, 548/348

[56] References Cited

U.S. PATENT DOCUMENTS 3,379,529  4/1968  Porter et al. .................. 430/452
3,833,606  9/1974  Mohan ........................... 548/371
4,308,336 12/1981  Waki et al. ..................... 430/544

Primary Examiner—Henry R. Jiles
Assistant Examiner—J. G. Mullins
Attorney, Agent, or Firm—Sughrue, Mion, Zinn, Macpeak & Seas

[57] ABSTRACT

A photographic development inhibitor releasing compound of the formula (I):

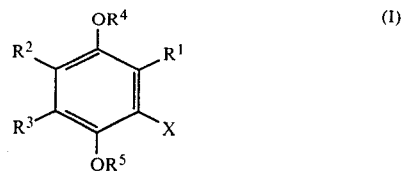

wherein X is an indazole residue which may be substituted and which is bonded to the benzene nucleus through the nitrogen atom at the 1-position or 2-position thereof; $R^1$, $R^2$ and $R^3$, which may be the same or different, are each hydrogen, an alkyl group, an aryl group, an alkylthio group, an arylthio group, a halogen atom, a hydrogen group, an alkoxy group, an aryloxy group, an acyl group, an alkoxycarbonyl group, an amido group, a sulfonamido group, a carbamoyl group, a sulfamoyl group, a heterocyclic residue or any of the groups described above for X; further $R^2$ and $R^3$ may combine with each other to form a ring; and $R^4$ and $R^5$, which may be the same or different, are each hydrogen or a group capable of being hydrolyzed in the presence of an alkali. The compound is very active and rapidly releases a development inhibiting agent upon oxidation. However, it is stable when it is incorporated into a silver halide emulsion layer and can be advantageously used in a photographic light-sensitive material.

2 Claims, No Drawings

PHOTOGRAPHIC DEVELOPMENT INHIBITOR (1H- OR 2H-) INDAZOLYL HYDROQUINONE DERIVATIVES

This is a division of application Ser. No. 259,278, Apr. 30, 1981, now U.S. Pat. No. 4,345,024.

FIELD OF THE INVENTION

The present invention relates to a novel photographic additive capable of oxidatively releasing a development inhibitor during development.

BACKGROUND OF THE INVENTION

Compounds that release a development inhibitor depending upon the density of the image at the time of development of a silver halide photographic light sensitive material (so-called DIR) are known. Examples of known DIR compounds are DIR hydroquinone derivatives as described in U.S. Pat. Nos. 3,379,529 and 3,620,746, and Japanese Patent Application (OPI) No. 129536/74. These DIR hydroquinones are, as described in the above patents, used for the purpose of attaining the so-called DIR effect, e.g., control of image tone, an improvement in graininess, image sharpness and color reproduction.

Although these DIR hydroquinones have desirable properties, they also have various defects. A first defect is that a sufficient DIR effect cannot be obtained because the compounds are not sufficiently active. A second defect is that incorporation of the compound into a light-sensitive emulsion layer as a dispersion deteriorates the storage stability of the light-sensitive material. A third defect is that synthesis of the compounds is not easy. A fourth defect is that poor storage stability of a coating solution containing the compound deteriorates the photographic properties.

SUMMARY OF THE INVENTION

It has now been found that the novel photographic DIR compounds according to the present invention are free from the above defects, and possess excellent properties.

An object of the present invention is to provide a novel photographic DIR compound.

Another object is to provide a photographic DIR compound which releases a development inhibitor immediately after being oxidized during development.

A further object is to provide a photographic DIR compound which does not reduce the storage stability of a light-sensitive material even though it is incorporated into the light-sensitive material.

Further another object is to provide a silver halide photographic material containing the photographic DIR compound.

Another object is to provide a photographic processing solution containing the novel photographic DIR compound.

A still further object is to provide a process for forming images by effecting development in the presence of the novel photographic DIR compound.

An even further object is to provide a novel photographic DIR compound which can be easily synthesized.

The objects are attained with photographic DIR compounds which release a development inhibitor after being oxidized and which are represented by the following formula (I)

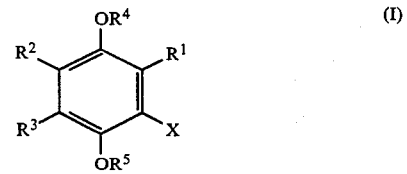

wherein X is an indazole residue which may be substituted and which is bonded to the benzene nucleus through the nitrogen atom at the 1-position or 2-position thereof; $R^1$, $R^2$ and $R^3$, which may be the same or different, are each hydrogen, an alkyl group, an aryl group, an alkylthio group, an arylthio group, a halogen atom, a hydroxy group, an alkoxy group, an aryloxy group, an acyl group, an alkoxycarbonyl group, an amido group, a sulfonamido group, a carbamoyl group, a sulfamoyl group, a heterocyclic residue or any of the groups described above for X; further $R^2$ and $R^3$ may combine with each other to form a ring; and $R^4$ and $R^5$, which may be the same or different, are each hydrogen or a group capable of being hydrolyzed in the presence of an alkali.

DETAILED DESCRIPTION OF THE INVENTION

The compounds represented by the formula (I) are described in greater detail below.

X represents an indazole residue which may be substituted and which is bonded to the benzene nucleus through the nitrogen atom at the 1-position or 2-position thereof. Suitable examples of substituents for the indazole residue include a nitro group, an amino group, a carboxy group, a cyano group, a halogen atom (for example, a bromine atom, a chlorine atom, etc.), a hydroxy group, an alkyl group (preferably an alkyl group having 1 to 12 carbon atoms, for example, a methyl group, an ethyl group, etc.), an alkoxy group (preferably an alkoxy group having 1 to 12 carbon atoms, for example, a methoxy group, an ethoxy group, etc.), an alkoxycarbonyl group (preferably an alkoxycarbonyl group having 2 to 13 carbon atoms, for example, an ethoxycarbonyl group, etc.), an alkylthio group (preferably an alkylthio group having 1 to 12 carbon atoms, for example, a methylthio group, an n-butylthio group, etc.), an acyl group (preferably an acyl group having an alkyl group having up to 11 carbon atoms, for example, an acetyl group, etc.), a sulfamoyl group (preferably a sulfamoyl group having an alkyl group having up to 30 carbon atoms, for example, a dimethylsulfamoyl group, etc.), a carbamoyl group (preferably a carbamoyl group having an alkyl group having up to 30 carbon atoms, for example, an N,N-dimethylcarbamoyl group, etc.), an amido group (preferably an amido group having an alkyl group having up to 11 carbon atoms, for example, an acetamido group, etc.), an acyloxy group (preferably an acyloxy group having having an alkyl group having up to 11 carbon atoms, for example, an acetoxy group, etc.), and the like. Of these substituents, a nitro group, a cyano group and a halogen atom are preferred.

Of the groups represented by X, an indazole group substituted with a nitro group at the 5-position thereof is most preferred in view of achieving the objects of the present invention.

In the formula (I), $R^1$, $R^2$ and $R^3$, which may be the same or different, each represents hydrogen, a halogen atom (for example, a chlorine atom, a bromine atom, an iodine atom, etc.), a hydroxy group, an alkyl group (preferably an alkyl group having 1 to 18 carbon atoms, for example, a methyl group, a tert-butyl group, a tert-octyl group, a pentadecyl group, etc.), an aryl group (for example, a phenyl group, a naphthyl group, etc.), an alkylthio group (preferably an alkylthio group having 1 to 18 carbon atoms, for example, a methylthio group, an octylthio group, a decylthio group, an octadecylthio group, etc.), an arylthio group (for example, a phenylthio group, etc.), an alkoxy group (preferably an alkoxy group having 1 to 18 carbon atoms, for example, a methoxy group, etc.), an aryloxy group (for example, a phenoxy group, etc.), an alkoxycarbonyl group (preferably an alkoxycarbonyl group having 2 to 19 carbon atoms, for example, an ethoxycarbonyl group, etc.), an acyl group (preferably an acyl group having an alkyl group having up to 17 carbon atoms, for example, an acetyl group, etc.), an amido group (preferably an amido group having an alkyl group having up to 17 carbon atoms, for example, an acetamido group, etc.), sulfonamido group (preferably a sulfonamido group having an alkyl group having up to 17 carbon atoms or a phenyl group, for example, a methanesulfonamido group, a benzenesulfonamido group, etc.), a carbamoyl group (preferably, a carbamoyl group having an alkyl group having up to 30 carbon atoms, for example, an N-methylcarbamoyl group, an N,N-dimethylcarbamoyl group, an N-dodecylcarbamoyl group, etc.), a sulfamoyl group (preferably a sulfamoyl group having an alkyl group having up to 30 carbon atoms, for example, a dimethylsulfamoyl group, etc.) or a heterocyclic residue (a saturated or unsaturated ring containing at least one nitrogen atom, a sulfur atom or an oxygen atom as a hetero atom, preferably a 5-membered or 6-membered ring, for example, an imidazolidin-1-yl group, etc.), or each represents any of the groups defined above for X. Of these groups, hydrogen, an alkyl group, an aryl group, an alkylthio group, a halogen atom, an alkoxy group, a carbamoyl group and X are preferred; and hydrogen, an alkyl group, an alkylthio group, an aryl group, and X are particularly preferred.

Further, $R^2$ and $R^3$ may combine with each other to form a saturated or unsaturated ring (for example, a naphthohydroquinone ring, a 5,6-tetramethylenehydroquinone ring, a 5,6-(1,3-cyclopentylenyl)hydroquinone ring, etc. when designated by including the hydroquinone mother nuclei). The ring may have one or more substituents which are defined for $R^1$, $R^2$ and $R^3$ above.

In the formula (I), $R^4$ and $R^5$, which may be the same or different, each represents hydrogen or a group capable of being hydrolyzed under alkaline conditions (for example, a halogeno substituted acyl group such as a chloroacetyl group, a dichloroacetyl, etc., an alkoxycarbonyl group such as an ethoxycarbonyl group, etc., an aryloxycarbonyl group such as a phenoxycarbonyl group, etc., and the like). Of these groups, hydrogen is preferred.

Specific examples of the compounds represented by the formula (I) are set forth below but the present invention is not to be construed as being limited thereto.

Compound I-1

2-(5-Nitro-2-indazolyl)hydroquinone

Compound I-2

6-Methyl-2-(5-nitro-2-indazolyl)hydroquinone

Compound I-3

6-tert-Butyl-2-(5-nitro-2-indazolyl)hydroquinone

Compound I-4

2-(5-Nitro-2-indazolyl)-6-tert-octylhydroquinone

Compound I-5

3,5,6-Trimethyl-2-(5-nitro-2-indazolyl)hydroquinone

Compound I-6

2-(5-Nitro-2-indazolyl)-6-pentadecylhydroquinone

Compound I-7

2-(6-Nitro-2-indazolyl)hydroquinone

Compound I-8

2-(4-Nitro-2-indazolyl)hydroquinone

Compound I-9

2-(7-Nitro-2-indazolyl)hydroquinone

Compound I-10

2-(5-Nitro-2-indazolyl)-5,6-tetramethylenehydroquinone

Compound I-11

5,6-(1,3-Cyclopentylenyl)-2-(5-nitro-2-indazolyl)hydroquinone

Compound I-12

5-Decylthio-2-(5-nitro-2-indazolyl)hydroquinone

Compound I-13

5-Dodecylthio-2-(5-nitro-2-indazolyl)hydroquinone

Compound I-14

2-(5-Nitro-2-indazolyl)-5-octadecylthiohydroquinone

Compound I-15

2-(5-Nitro-2-indazolyl)-6-phenylhydroquinone

Compound I-16

2-(5-Nitro-2-indazolyl)-5-phenylthiohydroquinone

Compound I-17

5-Chloro-2-(5-nitro-2-indazolyl)hydroquinone

Compound I-18

5-Methoxy-2-(5-nitro-2-indazolyl)hydroquinone

Compound I-19

2-(2-Indazolyl)hydroquinone

Compound I-20

2-(1-Indazolyl)hydroquinone

Compound I-21

2-(5-Chloro-2-indazolyl)hydroquinone

Compound I-22

2-(6-Dimethylsulfamoyl-2-indazolyl)hydroquinone

Compound I-23

2-(5-Cyano-2-indazolyl)hydroquinone

Compound I-24

2-(5-Methyl-2-indazolyl)hydroquinone

Compound I-25

2-(5-Methyl-1-indazolyl)hydroquinone

Compound I-26

2-(5-Nitro-2-indazolyl)naphthohydroquinone

Compound I-27

2,5-Bis(5-nitro-2-indazolyl)hydroquinone

Compound I-28

1,4-Diacetoxy-2-(5-nitro-2-indazolyl)benzene

Compound I-29

1,4-Bischloroacetoxy-2-(5-nitro-2-indazolyl)benzene

Compound I-30

2,3-Bis(5-nitro-1-indazolyl)-1,4-naphthohydroquinone

Compound I-31

2,3,5,6-Tetraquis(5-nitro-1-indazolyl)hydroquinone

Compound I-32

3-(N-Hexylcarbamoyl)-2-(5-nitro-1-indazolyl)-1,4-naphthohydroquinone

Compound I-33

3-(N-Dodecylcarbamoyl)-2-(5-nitro-1-indazolyl)-1,4-naphthohydroquinone

Compound I-34

2-(5-Nitro-1-indazolyl)-3-(N,N-tetramethylenecarbamoyl)-1,4-naphthohydroquinone

Of these compounds, Compounds I-1, I-3, I-12, I-15, I-18, I-27, I-28 and I-30 are preferred; and Compounds I-1 and I-3 are particularly preferred.

The compounds represented by the formula (I) can be generally synthesized in the following two different methods. The first method comprises reacting a benzoquinone or naphthoquinone derivative with an indazole derivative in a halogenated hydrocarbon such as chloroform, 1,2-dichloroethane, carbon tetrachloride, methyl chloroform, etc. at a temperature ranging from room temperature to 100° C. in the presence of an acid catalyst such as p-toluenesulfonic acid, benzene sulfonic acid, methanesulfonic acid, trifluoromethanesulfonic acid, etc. The second method comprises reacting a benzoquinone or naphthoquinone derivative substituted with a chlorine atom, a bromine atom or an iodine atom with an indazole derivative in an aprotic polar solvent such as acetone, tetrahydrofuran, dimethylformamide, etc. at a temperature ranging from room temperature to 100° C. in the presence of a base such as a potassium carbonate, sodium hydrogen carbonate, sodium hydroxide, etc. to obtain a quinone derivative and reducing the latter with a reducing agent such as diethylhydroxylamine, sodium hydrosulfite, etc. [These methods are taught within: Research Disclosure No. 18227 (1979) and Liebigs Ann. Chem., Vol. 764, page 131 (1972) which are incorporated herein by reference].

The benzoquinone derivative which is a starting material can be synthesized by the methods described, for example, in U.S. Pat. Nos. 2,899,334 and 3,700,453, British Pat. Nos. 557,750 and 557,802, U.S. Pat. Nos. 3,043,690, 2,616,893 and 3,009,958, Helv. Chem. Acta., Vol. 30, Page 578 (1947), J. Org. Chem., Vol. 22, page 772 (1957) and the reference cited therein, which are incorporated herein by reference. Also, the indazole derivative can be synthesized by the methods described, for example, in Org. Syn. Coll. Vol., Vol. 3, page 660 (1955), Synthesis, page 375 (1972), Ber., Vol. 55, page 1139 (1922), J. Chem. Soc., page 2735 (1960), Ann., Vol. 478, page 154 (1930), Ber., Vol. 43, page 2543 (1910), Ann. Chem., Vol. 681, page 45 (1965), Ber., Vol. 53B, page 1211 (1920), J. Prakt. Chem., Vol. 118, page 75 (1928), Liebigs Ann. Chem., Vol. 586, page 84 (1954), Heterocyclic Compounds, Bd 5, pages 162–192, John Wiley & Sons, New York (1957) and the references cited therein, which are incorporated herein by reference.

Specific synthesis methods of the compounds according to the present invention are illustrated below.

Synthesis of Compound I-1

To a mixture of 23.8 g of p-benzoquinone, 32.6 g of 5-nitro-1H-indazole and 250 ml of chloroform, 40 g of p-toluenesulfonic acid was added with stirring. After reacting at 60° C. for 6 hours, 500 ml of water was added to the reaction mixture and the resulting raw crystals were collected by filtration. The raw crystals were disclosed in 200 ml of dimethylformamide and the solution was filtered. To the filtrate, 800 ml of acetonitrile was added and the products thus formed were collected by filtration to obtain 37.6 g (Yield: 69%) of the desired compound which was a brown amorphous product. The melting point was around 250° C. (The definite melting point was not observed).

Synthesis of Compound I-3

To a mixture of 16.4 g of tert-butyl-p-benzoquinone, 16.3 g of 5-nitro-1H-indazole and 200 ml of chloroform, 20 g of p-toluenesulfonic acid was added with stirring. After reacting at 25° C. for two days, 500 ml of water was added to the reaction mixture and the resulting crystals were collected by filtration. By fractional recrystallization using 1.4 liter of methanol, 9.8 g (Yield: 30%) of the desired compound which was an orange needle-like crystal was obtained. The melting point was 250° to 254° C.

Synthesis of Compound I-12

To a mixture of 28 g of 5-decylthio-p-benzoquinone, 16.3 g of 5-nitro-1H-indazole and 150 ml of chloroform, 20 g of p-toluenesulfonic acid was added with stirring. After reacting at 60° C. for 5 hours, 500 ml of water was added to the reaction mixture and the solid was separated by filtration. The chloroform layer was separated from the filtrate and concentrated. The residue was separated and purified by silica gel column chromatography (using toluene as a spreading agent) to obtain 4.3 g (Yield: 10%) of the desired compound which was a brown flake-like crystal. The melting point was 118° to 122° C.

Synthesis of Compound I-27

5.4 g of Compound I-1 and 11.6 g of manganese dioxide were refluxed with heating in 200 ml of acetone for 2 hours and reacted. The reaction mixture was filtered still hot to remove manganese dioxide which was washed with warm acetone. The filtrate was concentrated, methanol was added thereto and the resulting crystals were collected to yield 3.5 g (The melting point was 191° to 194° C.). The thus obtained benzoquinone derivative, 2.1 g of 5-nitro-1H-indazole and 2.9 g of p-toluenesulfonic acid were reacted in 50 ml of chloroform by refluxing with heating for 3 days. 500 ml of water was added to the reaction mixture and the resulting products were collected by filtration. By recrystallization form 120 ml of acetone, 3 g (Yield: 53%) of the desired compound which was a yellow amorphous product was obtained. The melting point was 270° to 272° C. (decomp.).

Synthesis of Compound I-30

To a mixture of 18.5 g of 2,3-dichloro-1,4-naphthoquinone, 26.6 g of 5-nitro-1H-indazole and 750 ml of acetone, 40.5 g of potassium carbonate were added with stirring at room temperature. After reacting at room temperature for 1.5 hours, the mixture was filtered. To the filtrate, 10.9 g of diethylhydroxylamine was added and the mixture was reacted at room temperature for 2 hours. 40 ml of 30% sulfuric acid was added to the mixture and the mixture was decanted. After adding 200 ml of methanol, the mixture was refluxed by heating and the resulting crystals were collected by filtration. The crystals were dissolved in 500 ml of acetone and the solution was concentrated. 150 ml of chloroform was added to the residue and the resulting crystals were collected by filtration to obtain 25 g (Yield: 64%) of the desired compound which was a yellow-brown amorphous product). The melting point was 227° to 228° C. (decomp.).

The photographic DIR compounds of the present invention can be incorporated into either a photographic emulsion layer or a developer. Where the photographic DIR compounds of the present invention are incorporated into the photographic emulsion layer to provide anti-diffusion properties thereto, all of the known ballast groups can be used. These ballast groups are described in many patents, e.g., U.S. Pat. Nos. 2,920,961, 3,926,634, 3,891,445, etc.

It is anticipated that the novel DIR compounds of the present invention are, as are the DIR hydroquinones described in U.S. Pat. No. 3,379,529, etc., subjected to cross-oxidation through a redox reaction thereof and the developing agent oxidants imagewise produced at the time of development, thereby imagewise releasing development inhibiting materials and being converted into colorless oxidants. Herein, the development inhibiting materials imagewise released cause intra-image effect and inter-image effect in the light-sensitive material, and exhibit DIR effects, e.g., an improvement in graininess, a softening of image tone, an improvement in image sharpness and an improvement in color reproduction, etc. It is quite surprising that the DIR compounds of the present invention are highly active and that almost no reduction in sensitivity with time occurs, as compared with the conventional DIR hydroquinones. Furthermore, it is surprising that the photographic DIR compounds of the present invention do not cause a reduction in sensitivity of the photographic emulsion, but have somewhat of a sensitizing tendency.

The photographic DIR compounds of the present invention can be used not only in a light sensitive material subjected to black-and-white development but also in a light-sensitive material for forming color images. Although the amount of the compound employed is not particularly limited, a preferred range is from $10^{-4}$ mol to 1 mol per mol of silver and a particularly preferred range is from $10^{-3}$ mol to $10^{-1}$ mol per mol of silver.

The silver halide photographic emulsions used together with the photographic DIR compounds of the present invention are those prepared by dispersing a light-sensitive silver halide such as silver chloride, silver bromide, silver chlorobromide, silver chloroiodide, silver iodobromide, and silver chloroiodobromide in a hydrophilic polymer material such as gelatin in the form of colloidal particles. The emulsions can be produced by various methods as described, for example, in Glafkides, *Chemie et Photographique,* Paul Montel; Zelikman, *Making and Coating Photographic Emulsion,* The Focal Press (1964); H. Frieser Ed., *Die Grundlagen der Photographischen mit Silberhalogeniden,* Akademishe Verlangsgesellschaft (1968), etc. To the silver halide photographic emulsion can be added various well-known additives such as chemical sensitizers, stabilizers, anti-fogging agents, hardeners, spectral sensitizers, surface active agents, and the like, which are usually added to conventional silver halide photographic emulsions. The photographic emulsion can be coated on a suitable support using well-known methods as described, for example, in Glafkides, *Chemie et Photographique,* Paul Montel; Zelikman, *Making and Coating Photographic Emulsion,* The Focal Press (1964); H. Frieser Ed., *Die Grundlagen der Photographischen mit Silberhalogeniden,* Akademishe Verlangsgesellschaft (1968), etc.

The photographic DIR compounds of the present invention can be dispersed and incorporated into a photographic layer using known methods as described, for example, in U.S. Pat. Nos. 2,322,027, 2,801,171, 3,425,835, 3,570,818, 3,773,302, 3,850,643, etc. In this case, they can be used individually or in admixture with each other. The photographic DIR compounds of the present invention can be used in combination with couplers and added to the same emulsion layer as the coupler, or added to auxiliary photographic layers such as an intermediate layer and the like as independent dispersions.

The photographic DIR compounds of the present invention are incorporated in the photographic element in an amount of 0.1 to 50 mol%, preferably 0.3 to 15 mol%, based upon the coupler(s) contained in each of the light-sensitive layers in which the DIR compound is incorporated: yellow coupler in the blue-sensitive layer, magenta coupler in the green-sensitive layer, or cyan coupler in the red-sensitive layer.

Color-forming couplers which can be used in the present invention include those compounds listed below. These couplers may be either four-equivalent or two-equivalent. Also, they can be either colored couplers for color correction or couplers (DIR couplers) releasing development inhibiting agents.

As yellow image-forming couplers, known open-chain ketomethylene based couplers can be used. Of these couplers, benzoylacetanilide based and pivaloylacetanilide based compounds are particularly useful. Representative examples of the yellow image-forming couplers which can be used in the present invention are described in U.S. Pat. Nos. 2,875,057, 3,265,506, 3,341,331, 3,369,895, 3,408,194, 3,551,155, 3,582,322, 3,725,072, West German Patent Publication No. 1,547,868, West German Patent Application (OLS) Nos. 2,057,941, 2,162,899, 2,213,461, 2,219,917, 2,261,361, 2,263,875, etc.

As the magenta image-forming couplers, pyrazolone based compounds, indazolone based compounds, cyanoacetyl compounds, and the like can be used. Of these compounds, the pyrazolone based compounds are particularly useful. Representative examples of the magenta image-forming couplers which can be used in the present invention are described in U.S. Pat. Nos.

2,439,098, 2,600,788, 2,983,608, 3,311,476, 3,419,391, 3,519,429, 3,558,319, 3,582,322, 3,615,506, British Pat. No. 956,261, West German Pat. No. 1,810,464, West German Patent Application (OLS) Nos. 2,408,665, 2,418,959, 2,424,467, Japanese Patent Publication No. 2016/69, etc.

As the cyan image-forming couplers, phenol derivatives, naphthol derivatives, and the like can be used. Representative, preferred examples of these compounds are described in U.S. Pat. Nos. 2,369,924, 2,434,272, 2,474,293, 2,600,788, 2,698,794, 2,706,684, 2,895,826, 3,034,892, 3,214,437, 3,253,924, 3,311,476, 3,386,830, 3,458,315, 3,560,212, 3,582,322, 3,583,971, 3,591,383, West German Patent Application (OLS) Nos. 2,163,811, 2,414,006, Japanese Patent Publication Nos. 6031/65, 28836/70, etc.

The colored couplers which can be used in the present invention are described in Japanese Patent Publication No. 2016/69, U.S. Pat. Nos. 2,434,272, 3,476,560, 3,476,564, West German Patent Application (OLS) No. 2,418,959 (magenta image-forming); and Japanese Patent Publication Nos. 22335/63, 20591/66, 11304/67, 32461/69, U.S. Pat. Nos. 3,034,892, 3,386,830 (cyan image-forming), etc.

As the DIR couplers, those compounds having groups which form development inhibiting agents as coupling releasable groups can be used. Preferred examples of these compounds are described in U.S. Pat. Nos. 3,148,062, 3,214,437, 3,227,554, 3,253,924, 3,617,291, 3,622,328, 3,639,417, 3,701,783, 3,705,201, 3,770,436, 3,790,384, Japanese Patent Publication No. 28836/70, West German Patent Application (OLS) Nos. 2,414,006, 2,417,914, etc.

The above couplers, etc., can be incorporated into a single layer in admixture with each other in order to satisfy the properties required for a light-sensitive material, and alternatively one compound can be incorporated into two or more different layers.

Incorporation of the coupler can preferably be carried out using known methods, for example, the method described in U.S. Pat. No. 2,322,027. That is to say, the coupler is preferably dissolved in an organic solvent having a boiling point of not less than about 180° C., such as phthalic acid alkyl esters (e.g., dibutyl phthalate, dioctyl phthalate, and the like), trimellitic acid esters (e.g., tri-tert-octyl trimellitate), phosphoric acid esters (e.g., diphenyl phosphate, triphenyl phosphate, tricresyl phosphate, dioctyl butyl phosphate, and the like), citric acid esters (e.g., tributyl acetylcitrate), alkylamides (e.g., N,N-diethyllaurylamide, and the like), etc., or in an organic solvent having a boiling point of about 30° C. to 150° C., such as lower alkyl acetates, e.g., ethyl acetate, butyl acetate, ethyl propionate, sec-butyl alcohol, methyl isobutyl ketone, $\beta$-ethoxyethyl acetate, methyl Cellosolve acetate, and the like, and then dispersed in a hydrophilic colloid. The high boiling organic solvents and low boiling organic solvents can be used in admixture with each other.

Where the coupler has an acid group, such as a carboxylic acid group, a sulfonic acid group, or the like, the coupler can be incorporated into a hydrophilic colloid as an alkaline aqueous solution.

The color-image forming coupler is generally employed in an amount of about $2 \times 10^{-3}$ mol to about $5 \times 10^{-1}$ mol, preferably $1 \times 10^{-2}$ mol to $5 \times 10^{-1}$ mol, per mol of silver in the emulsion layer.

The photographic DIR compounds of the present invention can be used after being emulsified in combination with compounds having reducing activity. Preferred examples of the compounds having reducing activity are hydroquinone and its derivatives, catechol and its derivatives, aminophenol and its derivatives, ascorbic acid and its derivatives, and the like.

The photographic DIR compounds of the present invention particularly show the great effects when they are used in a green-sensitive emulsion layer containing a two-equivalent magenta coupler or in a red-sensitive emulsion layer containing a cyan coupler.

Conventional photographic processing methods can be used for processing a silver halide photographic light-sensitive material in the presence of the photographic DIR compound according to the present invention. Known processing solutions can be used. The processing temperature can be between about 18° C. and about 50° C., in general, but temperatures lower than about 18° C. or higher than about 50° C. may be used, if desired. Either a development processing for forming silver images (black-and-white photographic processing) or a color photographic processing comprising developing processing for forming dye images can be employed, as desired.

Suitable developing solutions which can be employed in the case of black-and-white photographic processing can contain known developing agents. Preferred examples of the developing agents are dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolines, ascorbic acid, heterocyclic compounds in which a 1,2,3,4-tetrahydroquinoline ring and an indolene ring are fused together as described in U.S. Pat. No. 4,067,872, and the like, either individually or in combination. In general, the developing solutions can additionally contain known preservatives, alkali agents, pH buffering agents, anti-fogging agents, etc., and, if necessary, can further contain solubilizing agents, color toning agents, developing accelerators, surface active agents, defoaming agents, water softeners, hardening agents, viscosity-imparting agents, etc.

Conventional fixing solutions can be employed. In addition to thiosulfates and thiocyanates, organic sulfur compounds known as fixing agents can be employed as fixing agents. The fixing solutions can also contain water-soluble aluminum salts as hardening agents.

Conventional methods of forming color images can be used. For example, a nega-posi method (e.g., as described in *Journal of the Society of Motion Picture and Television Engineers*, Vol. 61, pages 667–701 (1953)), a color reversal method which comprises developing with a developer containing a black-and-white developing agent to form a negative silver image, then subjecting the photographic material to at least one uniform exposure or to another appropriate fogging treatment, and subsequently performing color development to obtain positive dye images; a silver dye bleaching method which comprises exposing a dye-containing photographic emulsion layer and developing the same to form a silver image and then bleaching the dyes using the silver image as a bleaching catalyst; etc., can be employed.

The color developer generally comprises an alkaline aqueous solution containing a color developing agent. Suitable color developing agents which can be employed include known primary aromatic amine developing agents. Preferred examples of color developing agents are phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfamidoethylaniline, 4-amino-3-methyl-N-ethyl-N-β-methoxyethylaniline, etc.).

In addition, developing agents described in L. F. A. Mason, *Photographic Processing Chemistry*, at pages 226 to 229, Focal Press (1966), U.S. Pat. Nos. 2,193,015 and 2,592,364, Japanese Patent Application (OPI) No. 64933/73, etc., can be employed.

The color developers can also contain pH buffering agents, such as sulfites, carbonates, borates and phosphates of alkali metals, developing inhibitors or anti-fogging agents such as bromides, iodides or organic anti-fogging agents, etc. In addition, if desired, the color developers can also contain water softeners, preservatives such as hydroxylamine; organic solvents such as benzyl alcohol, diethylene glycol, etc.; developing accelerators such as polyethylene glycol, quaternary ammonium salts, amines; dye-forming couplers; competing couplers; fogging agents such as sodium borohydride; auxiliary developers such as 1-phenyl-3-pyrazolidone; viscosity-imparting agents; polycarboxylic acid type chelating agents described in U.S. Pat. No. 4,083,723; anti-oxidizing agents as described in West German Patent Application (OLS) No. 2,622,950; and the like.

The photographic emulsion layers after color development are generally bleach-processed. Bleach processing can be performed at the same time as fixing, or separately therefrom. Suitable bleaching agents which can be employed are compounds of polyvalent metals such as iron (III), cobalt (IV), chromium (VI), copper (II), etc., peracids, quinones, nitroso compounds, etc. Specific examples include ferricyanides; bichromates; organic complexes of iron (III) or cobalt (III), for example, complexes of aminopolycarboxylic acids such as ethylenediaminetetraacetic acid, nitrilotriacetic acid, 1,3-diamino-2-propanol tetraacetic acid, etc., complexes of organic acids such as citric acid, tartaric acid, malic acid, etc.; persulfates; permanganates; nitrosophenol; etc. Of these, particularly useful bleaching agents are potassium ferricyanide, sodium ethylenediaminetetraacetate iron (III) and ammonium ethylenediaminetetraacetate iron (III). Ethylenediaminetetraacetate iron (III) complex is useful both in a bleaching solution and in a mono bath bleach-fixing solution.

Bleaching and bleach-fixing solutions can contain various additives, including bleach accelerating agents as described in U.S. Pat. Nos. 3,042,520 and 3,241,966, Japanese Patent Publication Nos. 8506/70 and 8836/70, thioether compounds as described in Japanese Patent Application (OPI) No. 65732/78, and the like.

The photographic DIR compounds of the present invention can be used in various kinds of silver halide photographic light-sensitive materials, and they are useful either for black-and-white light-sensitive materials or for color light-sensitive materials. Also, they can be used in silver halide photographic light-sensitive materials having various applications, for example, black-and-white materials for general use, black-and-white materials for printing, X-ray recording materials, electron ray recording materials, black-and-white materials for high resolution, general color materials, color X-ray recording materials, diffusion transfer type color materials, etc.

An embodiment of the present invention can be a multi-layer color light-sensitive material. The material may be comprised of: a blue-sensitive emulsion layer unit composed of one or more silver halide emulsion layers containing a yellow image-forming coupler which is sensitive mainly to blue light (wavelength: not more than about 500 nm) and is capable of forming a yellow dye on coupling with an oxidized primary aromatic amino developing agent, a green-sensitive emulsion layer unit composed of one or more silver halide emulsion layers containing a magenta image-forming coupler which is sensitive mainly to green light (wavelength: about 500 to about 600 nm) and is capable of forming a magenta dye on coupling with an oxidized primary aromatic amino developing agent, and a red-sensitive emulsion unit composed of one or more silver halide emulsion layers containing a cyan image-forming coupler which is sensitive mainly to red light (wavelength: not less than about 590 nm) and is capable of forming a cyan dye on coupling with an oxidized primary aromatic amino developing agent; and which can include auxiliary photographic layers such as an intermediate layer and the like, the compounds of the present invention being incorporated into any of the above described emulsion layers or intermediate layers.

In the above embodiment, the emulsion layers forming the blue-sensitive emulsion layer unit, the green-sensitive emulsion layer unit, and the red-sensitive emulsion layer unit can be arranged in various orders depending upon the end-use application of the light-sensitive material. For instance, where each emulsion layer unit is composed of one emulsion layer, the red-sensitive emulsion layer, the green-sensitive emulsion layer, and the blue-sensitive emulsion layer can be present on the support in this order, or this order can be changed. Where any one of the emulsion layer units is composed of two or more emulsion layers, they can be adjacent to each other or they can be interposed between emulsion layers of other emulsion layer units.

A multi-layer color light-sensitive material is also useful which has on the support thereof a red-sensitive silver halide light-sensitive emulsion layer unit containing a non-diffusible uncolored cyan coupler and a non-diffusible colored cyan coupler capable of providing a cyan image through color development; a green-sensitive silver halide light-sensitive emulsion layer unit containing a non-diffusible uncolored magenta coupler and a non-diffusible colored magenta coupler capable of providing a magenta image; and a blue-sensitive silver halide light-sensitive emulsion layer unit containing a non-diffusible uncolored yellow coupler capable of providing a yellow image, in which the developing agents of the present invention are incorporated into the red-sensitive emulsion layer unit, the green-sensitive emulsion layer unit, and the blue-sensitive emulsion layer, or in intermediate layers.

Since the photographic DIR compounds of the present invention are very active, development inhibiting agents are released immediately after oxidation. Thus the addition of the photographic DIR compound of the present invention in a small amount enables achievement of excellent DIR effects, that is to say, control of image tone, improvement in graininess, image sharpness and color reproduction, etc. Furthermore, since the photographic developing agents of the present invention are stable even though they are present in the light-sensitive emulsion and do not degrade the storage stability of the light-sensitive material, they can be used without any concern. Moreover, the photographic DIR compounds of the present invention can be quite easily synthesized as shown in Preparation Examples above.

The present invention will be described in greater detail by reference to the following Examples although the invention is not intended to be construed to be limited thereto.

EXAMPLE 1

Preparation of Sample 101

1 Kg of a conventional silver iodobromide emulsion (amount of silver: 0.6 mol; content: 6 mol%) was subjected to spectral sensitization using $4\times10^{-5}$ mol per mol of silver of Sensitizing Dye I (set forth below) and $1\times10^{-5}$ mol per mol of silver of Sensitizing Dye II. 100 g of Coupler A was dissolved in 100 ml of tricresyl phosphate and 200 ml of ethyl acetate, and emulsified in 1 kg of a 10% gelatin aqueous solution using 4 g of sodium nonylbenzene sulfonate to produce Emulsion (I). 560 g of Emulsion (I) was added to 1 kg of the above spectrally sensitized silver iodobromide emulsion and stirred, to which 1.4 g of sodium 2,4-dichloro-6-hydroxy triazine as an aqueous solution thereof was added as a hardening agent. The thus-prepared coating solution was coated on a transparent cellulose triacetate film support so as to provide a silver coating amount of 1.5 g/m². Then a solution prepared by adding 2 g of sodium 2,4-dichloro-6-hydroxy triazine to 1 kg of a 10% aqueous gelatin solution was coated thereon to provide a protective layer having a dry film thickness of 1.5 microns.

Preparation of Samples 102 to 104 and 106

Samples 102, 103, 104 and 106 were produced in the same manner as Sample 101 except that Compounds I-3, (a), (b) and (c), respectively were further added to the tricresyl phosphate/ethyl acetate mixture of Emulsion (I) of Sample 101 in an amount of 10 mol% based upon Coupler A.

Preparation of Sample 105

Sample 105 was produced in the same manner as in Sample 101 except that Compounds (a) and (b) were further added to the tricresyl phosphate/ethyl acetate mixture of Emulsion (I) of Sample 101 in an amount of 10 mol% based upon Coupler A.

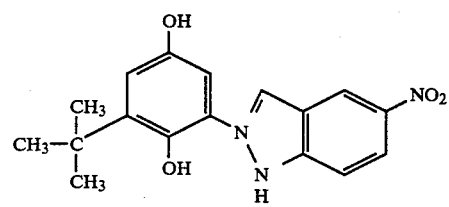

Compound I-3

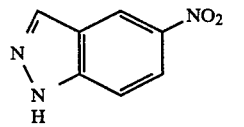

Compound (a)

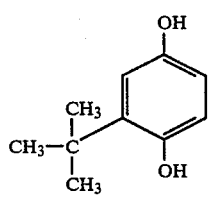

Compound (b)

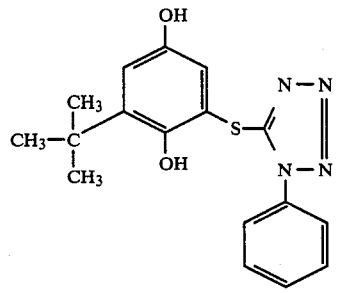

Compound (c)

Compounds used in preparing the above samples

Sensitizing Dye I

Anhydro-5,5'-dichloro-3,3'-di-sulfopropyl-9-ethyl-thiacarbocyanine hydroxide pyridinium salt

Sensitizing Dye II

Anhydro-9-ethyl-3,3'-di-(3-sulfopropyl)-4,5,4',5'-dibenzothiacarbocyanine hydroxide triethylamine salt

Coupler A 1-hydroxy-N-[γ-(2,4-di-tert-amylphenoxypropyl]-2-naphthamide

Samples 101 to 106 were subjected to stepwise exposure to red light and were then developed at 38° C. using the following steps.

1. Color Development—3 min and 15 sec
2. Bleaching—6 min and 30 sec
3. Water Washing—3 min and 15 sec
4. Fixing—6 min and 30 sec
5. Water Washing—3 min and 15 sec
6. Stabilizing—3 min and 15 sec The composition of the processing solutions used in each step was as follows:

Color Developer

Sodium Nitrilotriacetate—1.0 g
Sodium Sulfite—4.0 g
Sodium Carbonate—30.0 g
Potassium Bromide—1.4 g
Hydroxyamine Sulfate—2.4 g
4-[N-Ethyl-N-(β-hydroxyethyl)amino]-2-methyl-aniline Sulfate—4.5 g
Water to make—1 l

Bleaching Solution

Ammonium Bromide—160.0 g
Ammonia (28% aq. soln.)—25.0 ml
Sodium Ethylenediaminetetraacetatoferrate (III-)—130.0 g
Glacial Acetic Acid—14.0 ml
Water to make—1 l

Fixing Solution

Sodium Tetrapolyphosphate—2.0 g
Sodium Sulfite—4.0 g
Ammonium Thiosulfate (70% aq. soln.)—175.0 ml
Sodium Hydrogensulfite—4.6 g
Water to make—1 l

Stabilizing Solution

Formaldehyde (40% aq. soln.)—8.0 ml
Water to make—1 l

The optical density of Samples 101 to 106 thus processed was measured using red light. The characteristics obtained (relative sensitivity, gradation γ) are shown in Table 1 below.

TABLE 1

| Sample | Additive | Relative Sensitivity* | γ |
|---|---|---|---|
| 101 | — | 100 | 0.79 |
| 102 | I - 3 | 135 | 0.51 |
| 103 | (a) | 95 | 0.88 |
| 104 | (b) | 100 | 0.95 |
| 105 | (a) + (b) | 95 | 0.94 |
| 106 | (c) | 30 | 0.62 |

*The relative sensitivity is a relative value when the log E value corresponding to a density of fog + 0.2 in Sample 101 was regarded as 100.

From the results shown in Table 1 above, it can be seen that the sample containing Compound I-3 shows a higher sensitivity than the sample to which the compound is not added and has a markedly large effect of softening the gradation in comparison with the samples to which the known DIR hydroquinone, i.e., 2-tert-butyl-5-(1-phenyltetrazol-5-ylthio)hydroquinone was added.

Also, these samples were subjected to edge exposure using soft X-rays, to the above development processing, and to scanning using a microdensitometer through a red filter. As a result, it was found that the sample containing Compound I-3 showed a large edge effect as compared with the sample not containing the compound.

Furthermore, Samples 101, 102 and 106 were allowed to stand in a refrigerator at 10° C. for 3 days and separately allowed to stand in a room in which the temperature and humidity were respectively adjusted to 40° C. and 80% RH, for 3 days. The samples allowed to stand under different conditions described above were subjected to the same exposure, development processing, and density measurement as in Example 1.

The change in sensitivity between the sample allowed to stand in a refrigerator at 10° C. and the same sample allowed to stand under the high temperature and high humidity conditions for 3 days were measured and the results obtained are shown in Table 2. The change in sensitivity is indicated as ΔS(fog+0.2), i.e., the difference between the sample allowed to stand in a refrigerator and the sample allowed to stand under the high temperature and high humidity conditions in log E which corresponds to the optical density at fog+0.2 in the characteristic curve of the sample.

TABLE 2

| Sample | Additive | ΔS (fog + 0.2) |
|---|---|---|
| 101 | — | −0.05 |
| 102 | I - 3 | −0.06 |
| 106 | (c) | −0.15 |

As is apparent from the above results, the sample to which Compound I-3 was added, have good stability with time as a raw film (i.e., a less reduction in sensitivity) as compared to the sample to which the known DIR hydroquinone, i.e., 2-tert-butyl-5-(1-phenyltetrazol-5-ylthio)hydroquinone was added.

EXAMPLE 2

On a cellulose triacetate film support were coated in succession the first through eleventh layers having the compositions shown below to thus produce multi-layer color light-sensitive materials 201 to 204. The additives marked with an asterisk (*) are the same as in Example 1.

First Layer: Antihalation Layer (AHL)

A gelatin layer containing black colloidal silver

Second Layer: Intermediate Layer (ML)

A gelatin layer containing an emulsion of 2,5-di-tert-octylhydroquinone

Third Layer: First Red-Sensitive Emulsion Layer (RL$_1$)

Silver Iodobromide Emulsion (iodide: 5 mol%)
Silver Coating Amount: 1.79 g/m$^2$
Sensitizing Dye I*
  $6 \times 10^{-5}$ mol per mol of silver
Sensitizing Dye II*
  $1.5 \times 10^{-5}$ mol per mol of silver
Coupler A*
  0.04 mol per mol of silver
Coupler C-1
  0.0015 mol per mol of silver
Coupler C-2
  0.0015 mol per mol of silver
Compound I-3, I-15, I-18 or I-28
  0.002 mol per mol of silver Fourth Layer: Second Red-Sensitive Emulsion Layer (RL$_2$)

Silver Iodobromide Emulsion (iodide: 4 mol%)
Silver Coating Amount: 1.4 g/m$^2$
Sensitizing Dye I*
  $3 \times 10^{-5}$ mol per mol of silver
Sensitizing Dye II*
  $1.2 \times 10^{-5}$ mol per mol of silver
Coupler A*
  0.005 mol per mol of silver
Coupler C-1
  0.0008 mol per mol of silver
Coupler C-2
  0.0008 mol per mol of silver
Coupler C-3
  0.015 mol per mol of silver Fifth Layer: Intermediate Layer (ML)

Same as the Second Layer

Sixth Layer: First Green-Sensitive Emulsion Layer (GL$_1$)

Silver Iodobromide Emulsion (iodide: 4 mol%)
Silver Coating Amount: 1.5 g/m$^2$
Sensitizing Dye III*
  $3 \times 10^{-5}$ mol per mol of silver
Sensitizing Dye IV*
  $1 \times 10^{-5}$ mol per mol of silver
Coupler B*
  0.05 mol per mol of silver
Coupler M-1
  0.008 mol per mol of silver Seventh Layer: Second Green-Sensitive Emulsion Layer (GL$_2$)

Silver Iodobromide Emulsion (iodide: 5 mol%)
Silver Coating Amount: 1.6 g/m$^2$
Sensitizing Dye III*
  $2.5 \times 10^{-5}$ mol per mol of silver
Sensitizing Dye IV*
  $0.8 \times 10^{-5}$ mol per mol of silver Coupler B*
0.02 mol per mol of silver
Coupler M-1
0.003 mol per mol of silver Eighth Layer: Yellow Filter Layer (YEL)

A gelatin layer prepared by coating a coating solution containing yellow colloidal silver and a 2,5-di-tert-octylhydroquinone emulsion in a gelatin aqueous solution.

Ninth Layer: First Blue-Sensitive Emulsion Layer ($BL_1$)

Silver Iodobromide Emulsion (iodide: 6 mol%)
Silver Coating Amount: 1.5 g/m$^2$
Coupler Y-1
0.25 mol per mol of silver Tenth Layer: Second Blue-Sensitive Emulsion Layer ($BL_2$)

Silver Iodobromide Emulsion (iodide: 6 mol%)
Silver Coating Amount: 1.1 g/m$^2$
Coupler Y-1
0.06 mol per mol of silver Eleventh Layer: Protective Layer (PL)

Prepared by coating a gelatin layer which contained an emulsion of silver iodobromide super fine particles (amount of silver: 0.06 mol per kg; iodide content: 1.4 mol%; average particle size: 0.03μ), and polymethylmethacrylate particles (diameter: about 1.5μ).

To each layer were added a suitable amount of a gelatin hardener, a surface active agent, and a thickening agent in addition to the above components.

Sample 210

Sample 210 was prepared in the same manner as in Sample 201 except that Compound I-3 was not used.

Sample 220

Sample 220 was prepared in the same manner as in Sample 201 except that Compound (c) was used in place of Compound I-3.

Couplers used in preparing the samples

Coupler C-1: 1-Hydroxy-4-[2-(2-hexyldecyloxycarbonyl)phenylazo]-2-N-(1-naphthyl)naphthamide
Coupler C-2: 1-Hydroxy-4-[4-(ethyloxycarbonyl)phenylazo]-2-(N-dodecyl)naphthamide
Coupler C-3: 1-Hydroxy-4-iodo-2-(N-dodecyl)naphthamide
Coupler M-1: 1-(2,4,6-Trichlorophenyl)-3-hexadecanamido-4-(4-hydroxyphenyl)azo-5-pyrazolone
Coupler Y-1: α-(2,4-Dioxo-5,5-dimethyloxazolidinyl)-α-pivaloyl-2-chloro-5-[α-(2,4-di-tert-amylphenoxy)-butanamido-]acetanilide The thus-prepared samples were subjected to stepwise exposure using white light, blue light, green light, and red light sources, processing in the same manner as in Example 1 and sensitometry in the same manner as in Example 1.

It was found that Samples 201 to 204 showed a markedly large effect of softening the gradation and a small reduction in sensitivity in comparison with Sample 220.

The graininess of the cyan color images in these samples was determined using a RMS (Root Mean Square) method conventionally employed. The determination of graininess by the RMS method is well known by the one skilled in the art and described in an article of "RMS Granulality; Determination of Just-noticeable difference", *Photographic Science and Engineering*, Vol. 19, No. 4, pages 235 to 238 (1975).

The RMS value at the density of 1.0 of the samples was shown in Table 3 below. The results show that Samples 201 to 204 containing the DIR compounds according to the present invention has a small reduction in sensitivity and substantially same graininess in comparison with Sample 220 containing Comparison Compound (c).

TABLE 3

| Sample | Additive | Relative Sensitivity* | RMS |
|--------|----------|----------------------|-------|
| 201 | I - 3 | 98 | 0.009 |
| 202 | I - 15 | 95 | 0.010 |
| 203 | I - 18 | 98 | 0.011 |
| 204 | I - 28 | 90 | 0.010 |
| 210 | — | 100 | 0.013 |
| 220 | (c) | 70 | 0.009 |

*The relative sensitivity is a relative value when the log E value corresponding to a density of 1.0 in Sample 210 was regarded as 100.

While the invention has been described in detail and with reference to specific embodiments thereof, it will be apparent to one skilled in the art that various changes and modifications can be made therein without departing from the spirit and scope thereof.

What is claimed is:

1. A photographic development inhibitor releasing compound represented by the following formula (I):

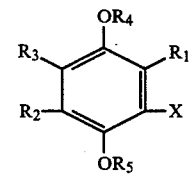

wherein X is an indazolyl group which may be substituted with a $NO_2$ group, a $NH_2$ group, a $CO_2H$ group, a CN group, a halogen atom, a hydroxy group, an alkyl group having 1 to 12 carbon atoms, an alkoxy group having 1 to 12 carbon atoms, an alkoxycarbonyl group having 2 to 13 carbon atoms, an alkylthio group having 1 to 12 carbon atoms, a lower alkanoyl group, —$SO_2NR_6R_7$, wherein $R_6$ and $R_7$ are independently hydrogen or alkyl having up to 30 carbon atoms, a —C(=O)$NR_6R_7$ group, wherein $R_6$ and $R_7$ are independently hydrogen or alkyl having up to 30 carbon atoms, a $NHCOR_{11}$ group where $R_8$ is an alkyl group having up to 8 carbon atoms, an alkanoyloxy group having up to 11 carbon atoms and which is bonded to the benzene nucleus through the nitrogen atom at the 1-position or 2-position thereof, $R_1$, $R_2$ and $R_3$, which may be the same or different, are each hydrogen, an alkyl group having 1 to 18 carbon atoms, a phenyl or naphthyl group, a halogen atom, a hydroxy group, an alkoxy group having 1 to 19 carbon atoms, a phenoxy group, a lower alkanoyl group, an alkoxycarbonyl group having 2 to 19 carbon atoms, a $NHCOR_9$ group where $R_9$ is an alkyl group having up to 17 carbon atoms, —$NHSO_2R_{10}$ where $R_{10}$ is an alkyl group having up to 17 carbon atoms, —$SO_2NR_6R_7$, wherein $R_6$ and $R_7$ are independently hydrogen or alkyl having up to 30 carbon atoms, an imidazolin-1-yl group or any of the groups described above for X; further $R_2$ and $R_3$ may combine with each other to form a ring which is a naphthohydroquinone ring, 5,6-tetramethylenehydroquinone ring or 5,6-(1,3-cyclopentylenyl)hydroquinone ring; and $R_4$ and $R_5$, which may be the same or different, are each hydrogen or a lower alkanoyl group substituted by halogen, a lower alkoxycarbonyl group or a phenoxycarbonyl group.

2. A photographic development inhibitor releasing compound represented by the following formula (I):

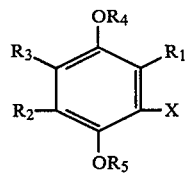

wherein X is a $NO_2$ substituted indazolyl group and which is bonded to the benzene nucleus through the nitrogen atom at the 1-position or 2-position thereof; $R_1$, $R_2$ and $R_3$, which may be the same or different, are each hydrogen, an alkyl group having 1 to 19 carbon atoms, a phenyl or naphthyl group, a halogen atom, a hydroxy group, an alkoxy group having 1 to 18 carbon atoms, a phenoxy group, a lower alkanoyl group, an alkoxycarbonyl group having 2 to 19 carbon atoms, a —NHCOR$_9$ group wherein $R_9$ is an alkyl group having up to 17 carbon atoms, —NHSO$_2$R$_{10}$ where $R_{10}$ is an alkyl group having up to 17 carbon atoms, —SO$_2$NR$_6$R$_7$, wherein $R_6$ and $R_7$ are independently hydrogen or alkyl having up to 30 carbon atoms, an imidazolin-1-yl group or any of the groups described above for X; further $R_2$ and $R_3$ may combine with each other to form a ring which is a naphthohydroquinone ring, a 5,6-tetramethylenehydroquinone ring or 5,6-(1,3-cyclopentylenyl)-hydroquinone ring; and $R_4$ and $R_5$, which may be the same or different, are each hydrogen or, a lower alkoxycarbonyl group or a phenoxycarbonyl group.

* * * * *